Aug. 8, 1972 T. G. HARCHARIK ET AL Plant Pat. 3,252
CARNATION PLANT
Filed Dec. 29, 1970
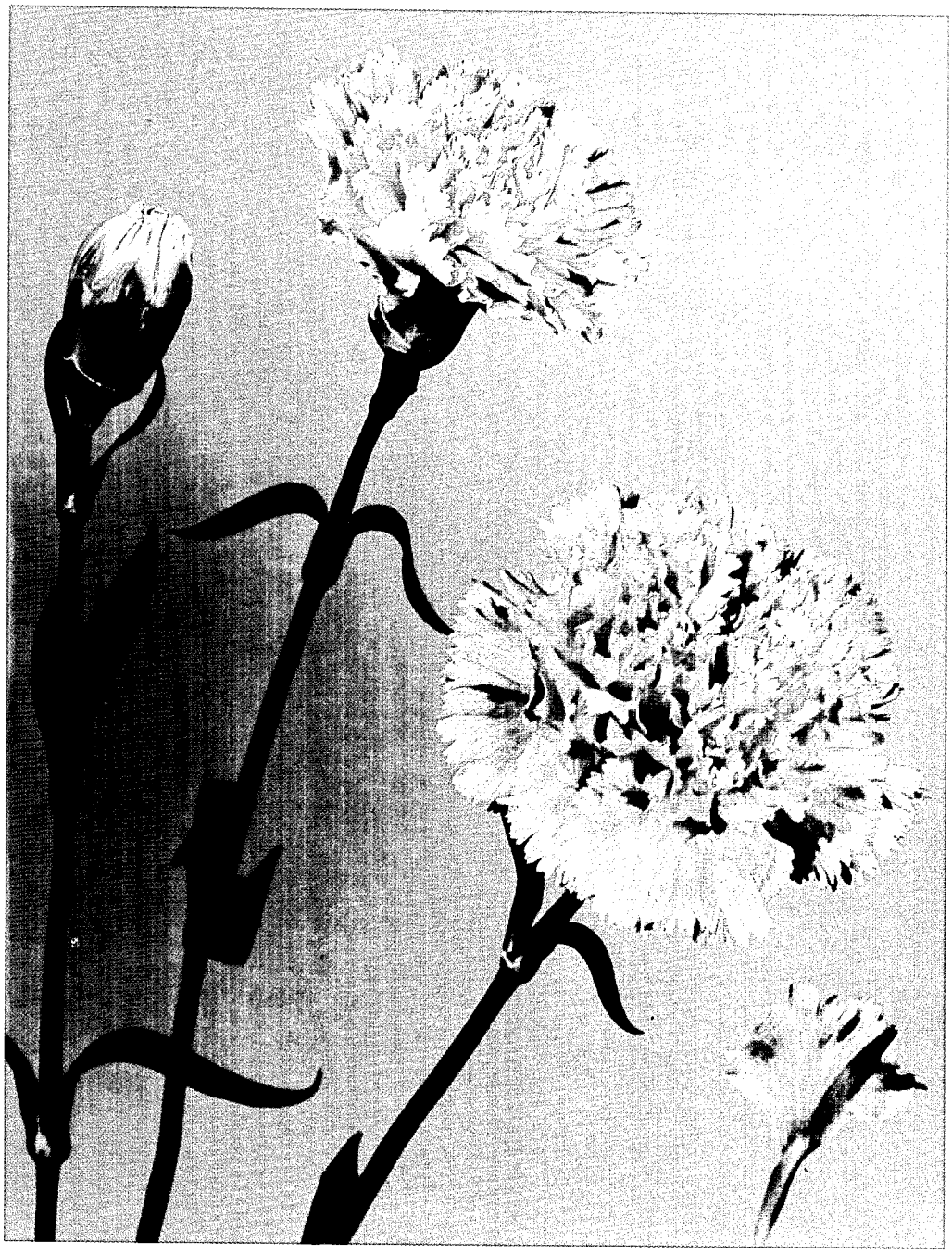
INVENTORS
THOMAS G. HARCHARIK,
WILLIAM E. DUFFETT
BY
Oberlin, Maky, Donnelly & Renner
ATTORNEYS

United States Patent Office

Plant Pat. 3,252

Patented Aug. 8, 1972

3,252
CARNATION PLANT

Thomas G. Harcharik, Salinas, Calif., and William E. Duffett, Akron, Ohio, assignors to Yoder Brothers, Inc., Barberton, Ohio

Filed Dec. 29, 1970, Ser. No. 102,567

Int. Cl. A01h *5/00*

U.S. Cl. Plt.—70 1 Claim

The present invention comprises a new and distinct cultivar of carnation plant which is a sport of the cultivar known in the United States as Orchid Beauty, U.S. Plant Patent No. 193, registered with the American Carnation Society on February 1936 by Littlefield-Wyman Nurseries.

The new cultivar is similar in many respects to Orchid Beauty, having the same characteristics of:

(1) Color.
(2) Size, diameter, and petal length.
(3) Form.
(4) Keeping and shipping quality.
(5) Height and stem length.
(6) Grade performance.
(7) Percentage of slab sided flowers produced under similar environmental conditions.

The new cultivar is distinguished from Orchid Beauty by the following characteristics:

(1) A faster rate of growth and response. Jet Beauty comes into flower, peaks, and produces a return crop up to 2 weeks earlier than the parent cultivar.

(2) It produces a significantly lower percentage of flowers with split calyxes under similar environmental conditions. Orchid Beauty produces a low of 3.27%; and a high of 9.83% splits. Jet Beauty under similar environmental treatment and planting dates produces a low of .27% and a high of 4.0% splits.

(3) It produces at least 2 flowers more per square foot per year under similar environmental conditions.

The new cultivar was selected from a flowering block of the parent cultivar at Salinas, Calif., and was asexually reproduced by cuttings at Salinas, Calif. The new cultivar has been found to retain its distinctive characteristics through successive propagations.

The accompanying drawing shows the unique characteristics of the new cultivar, the color being as nearly true as possible with color illustrations of this type.

The following detailed description is based on observations made of the new cultivar in a greenhouse in Salinas, California. The response time, blooming period, total vigor, and color may vary significantly with varying environmental conditions such as temperature, day length, and light intensity. Color references are to the Munsell Color Book, 1963 edition, and comparisons have been made with the cultivar Orchid Beauty. Where no comparative listings have been made, the listed values or description of Jet Beauty apply also to Orchid Beauty.

Botancial classification:

*Dainthus caryophyllus longicaulis*

| | Jet Beauty | Orchid Beauty |
|---|---|---|
| Bloom: | | |
| Type | Disbud | |
| Size (diam. in inches). | 3.0" at first crop harvest | |
| Petal edge | Lightly serrated | |
| Petal count | 65-70 at first crop harvest | 68-75 at first crop harvest. |
| Petal texture | Smooth | |
| Petal size: | | |
| Average length | 2¼" | |
| Average width | 1¼" | |
| Bud shape | Ovoid | |
| Splitting tendency [1] | .27% | 3.27%. |
| | 4.0% | 8.0%. |
| | 1.71% | 9.83%. |
| Slab tendency [1] | 2.34% | 2.03%. |
| | 1.00% | 1.00%. |
| | 3.43% | 4.20%. |

TABLE—Continued

| | Jet Beauty | Orchid Beauty |
|---|---|---|
| Bloom—Continued: | | |
| Keeping quality | 6.0 days | |
| Fragrance | Moderate, clove | |
| Color: | | |
| Center of flower | 7.5P8/4, purple | |
| Base of petals | 5G9/4, yellow green | |
| Edge or tip of petals. | 10P8/4, purple frosted | |
| Inside of petals | 3.75RP5/12, purple frosted | |
| Reserve of petals. | 2.5RP8/4, purple frosted | |
| Color stability | Good | |
| Seasonal variations. | None | |
| Reproductive organs: | | |
| Stamen, anthers | 5GY8/2 | |
| Stigma (2) | 5GY9/1 | |
| Styles (2) | 5GY9/1 | |
| Length | 1¼" | |
| Ovaries | 7.5GY8/4 | |
| Calyx: | | |
| Size | 1⅜" | |
| Shape | Tubular | |
| Number of sepals | 5 to 6 | |
| Stems: | | |
| Length | 24" | |
| Bending traits | 1 o'clock | |
| Plant: | | |
| Form | Erect and braching bush | |
| Growth | Vigorous, strong, sturdy, and upright. | |
| Height | 40" at first crop harvest | |
| Foliage: | | |
| Topside (color) | 10GY3/4, green | |
| Underside (color) | do | |
| Immature (color) | 10GY4/4, green | |
| Mature (color) | do | |
| Length: | | |
| Mature leaf | Length, 5"; width, ½" | |
| Shape | Long, narrow, curled | |
| Texture | Glaucous | |
| Displacement | Opposite | |

[1] Based on three separate twelve month flowering periods.

The following production data was obtained under controlled test flowering at Salinas, Calif. over a 2 year period of plant growth and flower evaluation. The grade standards used in the evaluations are as outlined by the Society of American Florists Grades and Standards.

| Production data | Jet Beauty | Orchid Beauty |
|---|---|---|
| Production per square foot—1 year: | | |
| A. July plantings (July 23) | 18.44 | 16.10. |
| B. June plantings (June 6) | 19.53 | 17.10. |
| C. July plantings, subsequent year (July 18). | 15.22 | 15.39. |
| First cut: | | |
| B | Oct. 24 | Oct. 28. |
| C | Jan. 7 | Jan. 15. |
| Peak of flower: | | |
| A | March 4 | March 15. |
| B | Nov. 9 | Nov. 13. |
| C | Jan. 19 | Jan. 22. |
| Split percentage: | | |
| A | 4% | 8%. |
| B | .27% | 3.27%. |
| C | 1.71% | 9.83%. |
| Slab percentage: | | |
| A | 1% | 1%. |
| B | 2.03% | 2.34%. |
| C | 3.43% | 4.20%. |
| Grade data: | | |
| Blue: | | |
| A | 31% | 35%. |
| B | 46.56% | 43.86%. |
| C | 23.71% | 17.04%. |
| Red: | | |
| A | 54% | 49%. |
| B | 39.57% | 40.00%. |
| C | 56.86% | 51.89%. |
| Green: | | |
| A | 11% | 7%. |
| B | 11.68% | 10.53%. |
| C | 14.29% | 17.04%. |

(References on following page)

We claim:

1. A new and distinct cultivar of carnation characterized particularly as to its uniqueness when compared to the parent cultivar Orchid Beauty by its faster rate of growth and response, coming into flower, peaking, and producing a return crop up to 2 weeks earlier than the parent cultivar, its production of a significantly lower percentage of flowers with split calyxes under similar environmental conditions, and its higher production of at least 2 flowers more per square foot per year under similar environmental conditions.

No references cited.

ROBERT E. BAGWILL, Primary Examiner

UNITED STATES PATENT OFFICE
CERTIFICATE OF CORRECTION

Patent No. PP-3,252 Dated August 8, 1972

Inventor(s) THOMAS G. HARCHARIK and WILLIAM E. DUFFETT

It is certified that error appears in the above-identified patent and that said Letters Patent are hereby corrected as shown below:

Column 2, line 8, after "Base of petals" the description should read --5GY9/4, yellow green--;
line 10, "Reserve" should be --Reverse--;
line 23, the description after "Form" should read --Erect and branching bush--;
approximately line 28, adjacent the heading "Mature" and under the heading "Jet Beauty", "do" should read --10GY3/4, green--.

Signed and sealed this 29th day of May 1973.

(SEAL)
Attest:

EDWARD M.FLETCHER,JR.
Attesting Officer

ROBERT GOTTSCHALK
Commissioner of Patents